US006418185B1

(12) United States Patent
Besson et al.

(10) Patent No.: US 6,418,185 B1
(45) Date of Patent: Jul. 9, 2002

(54) METHODS AND APPARATUS FOR TIME-MULTIPLEXING DATA ACQUISITION

(75) Inventors: Guy M. Besson, Wauwatosa, WI (US); Armin H. Pfoh, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/376,899

(22) Filed: Aug. 18, 1999

(51) Int. Cl.$^7$ ................................................. A61B 6/03
(52) U.S. Cl. ............................................. 378/19; 378/4
(58) Field of Search ................... 378/4, 19; 290/370.09, 290/370.11

(56) References Cited

U.S. PATENT DOCUMENTS

| | | | | |
|---|---|---|---|---|
| 4,514,628 A | * | 4/1985 | Frehaut et al. | ............... 250/299 |
| 5,041,729 A | * | 8/1991 | Takahashi et al. | ...... 250/370.11 |
| 5,430,785 A | | 7/1995 | Pfoh et al. | |
| 5,734,691 A | | 3/1998 | Hu et al. | |
| 5,761,267 A | | 6/1998 | Besson | |
| 5,764,720 A | | 6/1998 | Besson | |
| 5,845,003 A | | 12/1998 | Hu et al. | |
| 6,005,908 A | * | 12/1999 | Oppelt et al. | ................. 378/19 |
| 6,064,720 A | * | 5/2000 | Piscitelli et al. | ............. 378/154 |
| 6,108,575 A | | 8/2000 | Besson | |
| 6,173,029 B1 | | 1/2001 | Xie et al. | |

FOREIGN PATENT DOCUMENTS

| | | |
|---|---|---|
| EP | 0 982 682 A2 | 3/2000 |
| JP | 01063886 A * | 3/1989 |

OTHER PUBLICATIONS

US 6,055,290, 04/2000, Xie et al. (withdrawn)

* cited by examiner

*Primary Examiner*—David V. Bruce
(74) *Attorney, Agent, or Firm*—Carl B. Horton, Esq.; Armstrong Teasdale LLP

(57) ABSTRACT

A single-slice data acquisition system (DAS) for a CT imaging system is time-multiplexed to measure more than one signal over the DAS standard sampling time interval. In one embodiment, a detector element includes a scintillator and two photodiodes aligned with respective portions of the scintillator. Each photodiode generates a signal based on the scintillator output. The signal from one of the photodiodes is subjected to a time-dependent gain during consecutive sampling intervals. The gain-adjusted signal and the signal from the other photodiode are combined, and the combined signal is processed to obtain an estimate of the z-derivative of the signal. The estimated z-derivative is then used to generate a high quality image.

32 Claims, 3 Drawing Sheets

METHODS AND APPARATUS FOR TIME-MULTIPLEXING DATA ACQUISITION

BACKGROUND OF THE INVENTION

This invention relates generally to computed tomography (CT) imaging and, more particularly, to methods and apparatus for time-multiplexing data acquisition.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In a growing number of computer tomography applications it is desirable to increase the speed of data acquisition with corresponding increased patient coverage in a given amount of time. Demands increasingly are put upon the data acquisition system (DAS), particularly in multi-slice applications. To include a single-slice DAS row for each row of detectors is cost-prohibitive. It is known to use a single-slice DAS to process the signal of several combined detector rows. Although this approach may serve to limit the number of DAS systems needed, it negates the potential benefit of higher z-resolution through multiple rows in z.

BRIEF SUMMARY OF THE INVENTION

In one exemplary embodiment of the present invention, a single-slice imaging system DAS is time-multiplexed for measuring more than one signal during a DAS standard sampling time interval. More specifically, and in the one embodiment, each detector element includes a scintillator and two photodiodes aligned with respective portions of the scintillator. Each photodiode generates a signal based on the scintillator output. The signal from one of the photodiodes is subjected to a time-dependent gain during consecutive sampling intervals. The gain-adjusted signal and the signal from the other photodiode are combined, and the combined signal is processed to obtain an estimate of the z-derivative of the signal. The estimated z-derivative is then used to generate a high quality image.

DETAILED DESCRIPTION OF THE INVENTION

Figure 1:
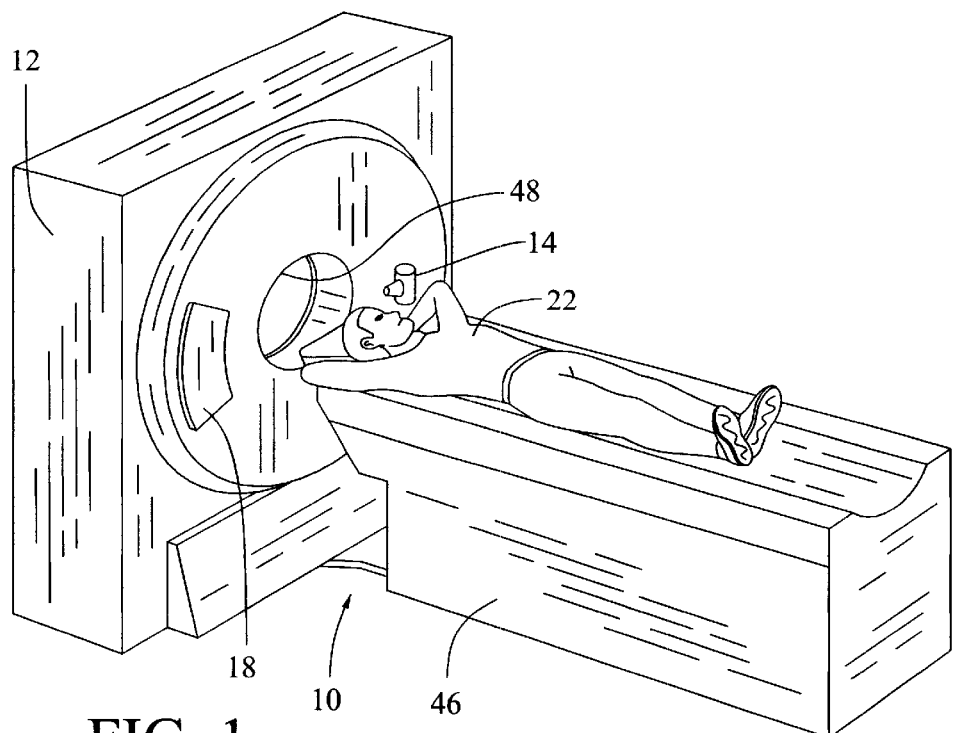
FIG. 1 is a pictorial view of a CT imaging system.
Figure 2:
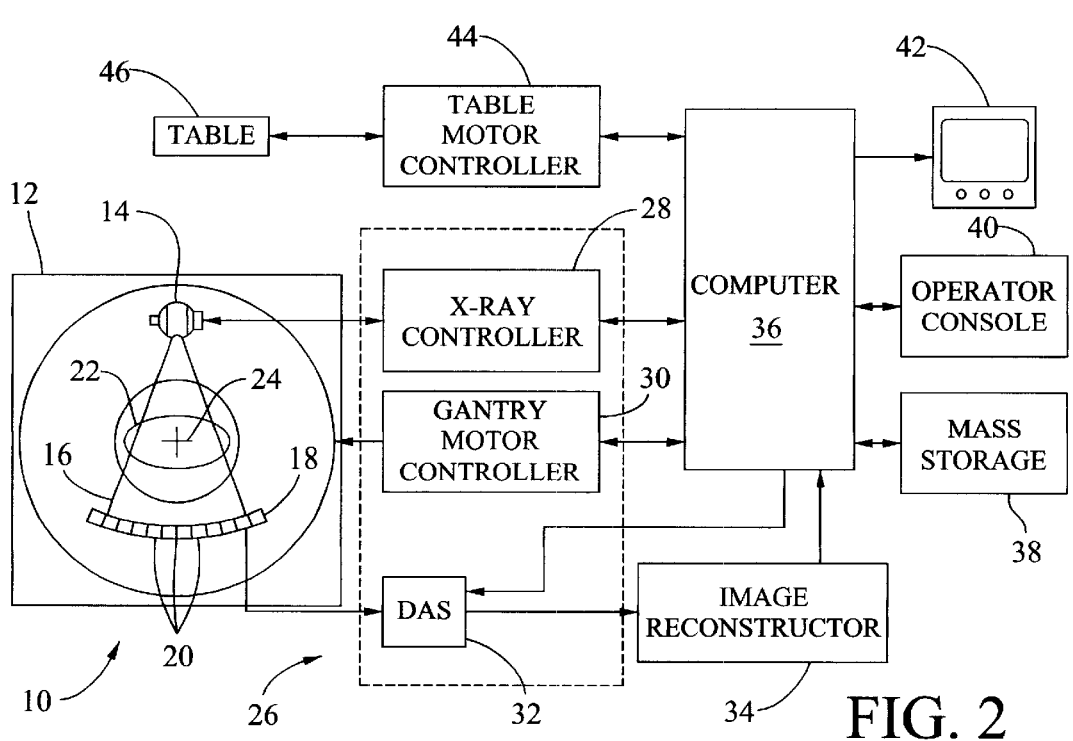
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through a medical patient 22. Detector array 18 is fabricated in a single slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
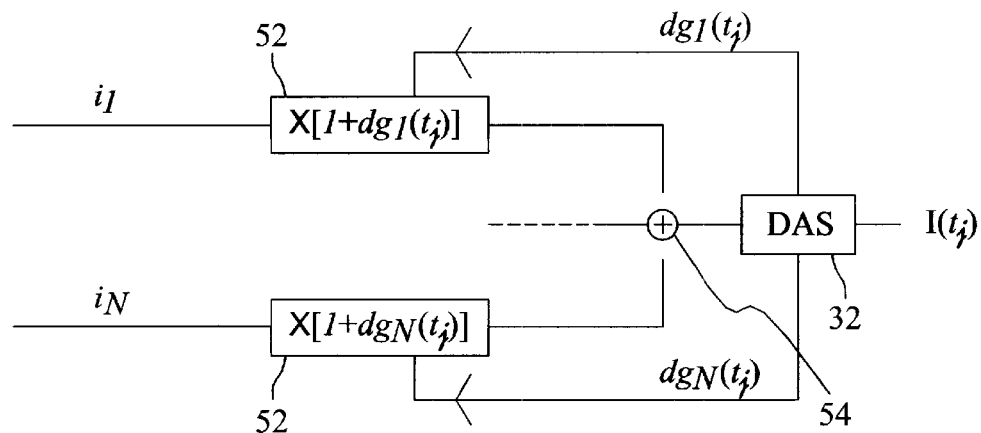
FIG. 3 is a block schematic diagram of a data acquisition system applying gain according to one embodiment of the present invention.

Referring to FIG. 3 and according to one embodiment of the invention, a DAS standard single slice sampling time is divided into N equal sub-intervals. $N^2$ time-dependent gains or gain offsets $dg_k(t_j)$, k=1, ... ,N; j=1, ... N are selected to be driven by DAS 32. Gains $dg_k(t_j)$ are supplied to multiplier 52. Signals $i_k$ are gain-adjusted and summed at adder 54. Each gain $dg_k(t_j)$ assumes up to N different values over each of the N sub-intervals. By sampling the DAS output N times over the standard single-slice sampling time, N signals $I_j$ are obtained which are described by the equation:

$$I_j = \sum_{k=1}^{k=N} i_k x[1 + dg_k(t_j)]$$

This equation is rewritten in the form of an N-by-N linear system:

$$[I_j]_{N\times 1} = [G]_{N\times N}[i_k]_{N\times 1} \text{ with: } G_{j,k} = [1 + dg_k(t_j)]$$

Dependent upon the selection of gains $1+dg_k(t_j)$, the matrix G is invertible and the inverse is stable, thus leading to:

$$[i_k]_{N\times 1} = [G]^{-1}_{N\times N}[I_j]_{N\times 1}$$

Accordingly, the N signals $i_k$, k=1, . . . N have been recovered.

Figure 4:
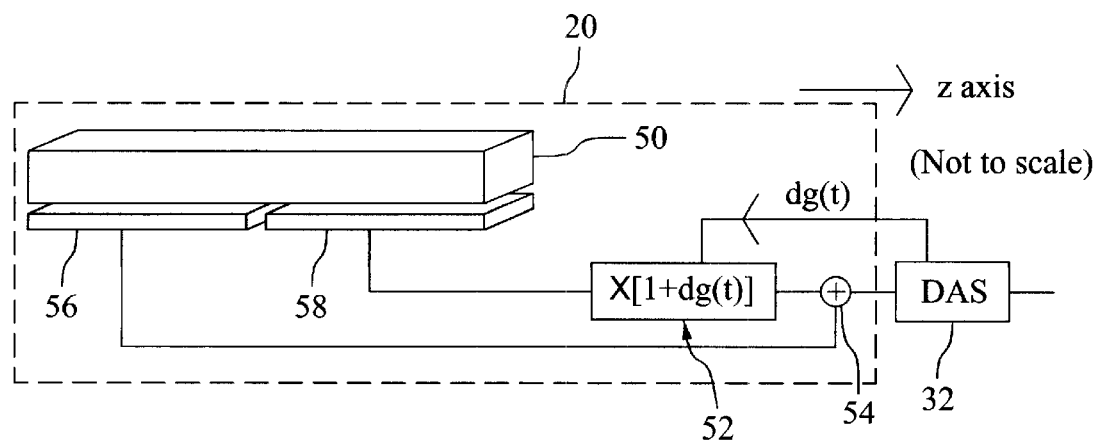
FIG. 4 is a block schematic diagram of a detector element according to one embodiment of the present invention.
Figure 5:
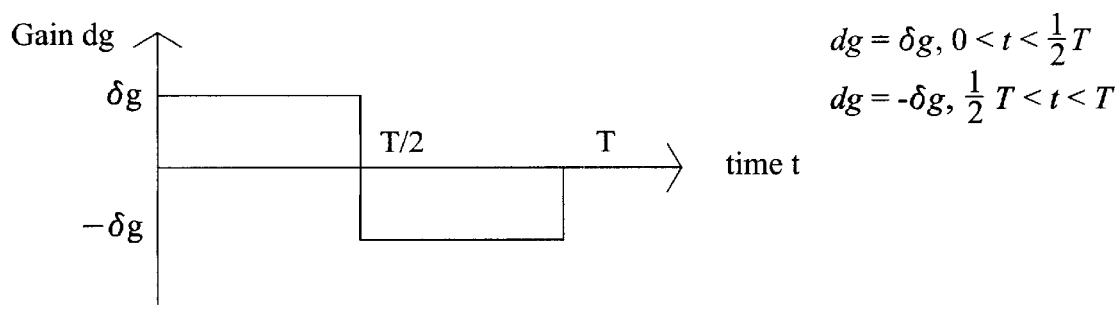
FIG. 5 is a graph showing time-dependent gain applied to intensity signals according to one embodiment of the present invention.

Referring to FIGS. 4 and 5, a detector element 20 includes, in one embodiment, a scintillator 50 and first and second photodiodes 56 and 58. Scintillator 50 is optically coupled to photodiodes 56 and 58. The signal transmitted by first photodiode 56 is combined, i.e., summed, at adder 54 with the gain-adjusted signal transmitted by second photodiode 58, and the combined signal is transmitted to DAS 32. DAS 32 samples the summed intensity projection signals.

For example, if the number of sub-intervals N is selected to be 2, gains $dg_1(t_1)$ and $dg_2(t_1)$ are set equal to $\delta g$, gains $dg_1(t_2)$ and $dg_2(t_2)$ are set equal to $-\delta g$, T represents the standard single slice sampling time, and, with the following time dependency for dg(t):

$$dg = \delta g, 0 < t < \frac{1}{2}T$$

$$dg = -\delta g, \frac{1}{2}T < t < T$$

two intensity measurements $I_1$ and $I_2$ are collected over time T. Measurements $I_1$ and $I_2$, to the first order, relate to the intensity I that would have been collected over T should $\delta g=0$ by:

$$I_1 \approx \frac{1}{2}I + \frac{1}{4}\delta g(I + \Delta z I'_z) \quad (1)$$

$$I_2 \approx \frac{1}{2}I - \frac{1}{4}\delta g(I + \Delta z I'_z)$$

where $\Delta z$ is a geometric factor that depends on cell length. Accordingly, by linear combination, the following relationships are obtained:

$$I \approx I_1 + I_2 \quad (2)$$

$$\Delta z I'_z \approx \frac{(I_1 - I_2)}{\frac{1}{2}\delta g} - (I_1 + I_2)$$

An estimate of the z-derivative of the intensity signal therefore is obtained by a processor, e.g., the image reconstructor 34 processor. In the reconstruction process, and by applying a higher order interpolation, it is possible to obtain either increased patient coverage by imaging at higher helical pitch while maintaining image quality, or improved image quality without increasing pitch.

Figure 6:
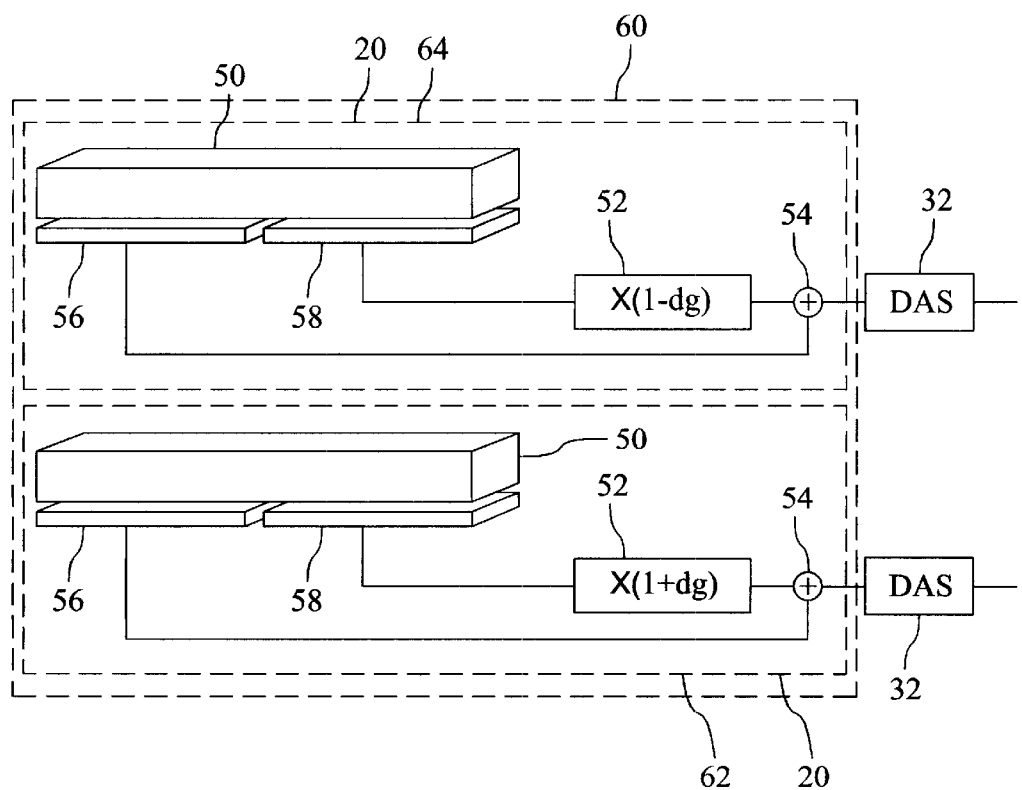
FIG. 6 is a block schematic diagram of a detector element pair according to one embodiment of the present invention.

Referring to FIG. 6, and in an alternative embodiment, a detector element pair 60 includes a first detector element 62 and a second detector element 64. The DAS sampling interval is kept at time T, but alternate gains of detector element pair 60 are determined as indicated in FIG. 6. Specifically, a positive gain dg is applied to intensity projection signals transmitted by first photodiode 56 of first detector element 62, and a negative gain dg is applied to intensity projection signals transmitted by first photodiode 56 of second detector element 64.

Benefits of using the above described embodiment include the absence of a need for a higher DAS sampling frequency and minimal hardware incremental costs. In one embodiment, gains $-dg$ and $+dg$ are fixed for the duration of the scan.

Since a sloped straight line is not affected by a z-convolution with an even kernel, to the extent that imaging occurs at the center $z_0$ of scintillator 50, and that the scintillator gain profile is even with respect to $z_0$, the fact that light photons are spread over several millimeters in z should not affect the ability to estimate the slope. A Taylor expansion of the signal around $z_0$ demonstrates that the foregoing proposition extends to all odd terms. Although even terms have their magnitude modified (symmetrically with respect to $z_0$), such terms do not introduce an error when modulated by linearly varying DAS gains.

The present invention is useful in improving image quality in axial scans, particularly for large apertures, and the signal z-slope information can be used to correct for partial volume errors. Gains $(1-dg)$ and $(1+dg)$ also can be applied respectively to intensity projection signals transmitted by two photodiodes of one detector element over the first T/2 sampling interval and switched respectively to $(1+dg)$ and $(1-dg)$ over the second T/2 sampling interval. In another embodiment, wherein DAS 32 sets dg=0, system 10 reverts to the usual single-slice operating mode. By keeping the DAS 32 double sampling rate, twice as many views are collected. From the z-derivative of the intensity signal, the z-derivative of the line-integral l(z) is:

$$l'(z)=I'(z)|I(z).$$

The algorithms described herein could be implemented in computer 36 or in image reconstructor 34. Also, it should be understood that system 10 is described herein by way of example only, and the invention can be practiced in connection with other types of imaging systems.

While the invention has been described in terms of various specific embodiments, those skilled in the art will recognize that the invention can be practiced with modification within the spirit and scope of the claims.

What is claimed is:

1. A method for time-multiplexing a data acquisition system in a computed tomography imaging system, the data acquisition system configured to sample intensity projection signals over a sampling time interval, said method comprising the steps of:

sub-dividing the sampling time interval into N sub-intervals;

sampling N intensity projection signals over each of the sub-intervals;

applying gains to the intensity projection signals being sampled over each sub-interval; and recovering $N^2$ intensity projection signals over the sampling time interval from the intensity projection signals affected by the gains.

2. A method in accordance with claim 1 wherein the step of applying gains to the intensity projection signals being sampled over each sub-interval comprises the step of applying $N^2$ gains over the sampling time interval.

3. A method in accordance with claim 1 wherein at least two of the gains are of approximately equal and constant magnitude.

4. A method in accordance with claim 1 wherein the step of recovering $N^2$ intensity projection signals over the sampling time interval from the intensity projection signals affected by the gains comprises the step of obtaining intensity projection signals in accordance with:

$$I_j = \sum_{k=1}^{k=N} i_k x [1 + dg_k(t_j)]$$

where $i_k$ is one of the N intensity projection signals sampled over one of the N sub-intervals, $dg_k(t_j)$ is the gain applied to intensity projection signal $i_k$, and $I_j$ is a total intensity projection signal obtained over one of the N sub-intervals.

5. A method in accordance with claim 4 wherein the step of recovering $N^2$ intensity projection signals over the sampling time interval from the intensity projection signals affected by the gains further comprises the step of recovering $N^2$ intensity projection signals in accordance with:

$$[I_j]_{N \times 1} = [G]_{N \times N} [i_k]_{N \times 1} \text{ with: } G_{j,k} = [1 + dg_k(t_j)][i_k]_{N \times 1} = [G]^{-1}_{N \times N} [I_j]_{N \times 1}$$

where $I_j$ is one of N total intensity projection signals obtained over the sampling time interval, [G] represents the gains applied over the sampling time interval, and $i_k$ is one of the N intensity projection signals sampled over one of the N sub-intervals.

6. An imaging system comprising at least one detector element and a data acquisition system, said detector element comprising a scintillator and a first photodiode and a second photodiode, said scintillator optically coupled to said photodiodes, said data acquisition system configured to sample intensity projection signals from at least one said detector element and to apply, over a sampling time interval, at least one gain to intensity projection signals transmitted by at least one of said photodiodes, said gains comprising at least one positive gain offset, at least one negative gain offset, and a zero gain offset.

7. A system in accordance with claim 6 further comprising a processor configured to determine z-derivative values from intensity projection signals after said data acquisition system has applied said gains.

8. A system in accordance with claim 6 wherein, for at least one said detector element, said photodiodes transmit intensity projection signals over said sampling time interval and said data acquisition system applies said gains to intensity projection signals sampled from said detector element over at least a portion of said sampling time interval.

9. A system in accordance with claim 8 wherein:
said detector elements comprise at least one detector element pair, each said detector element pair comprising a first detector element and a second detector element; and
for at least one said detector element pair and for the duration of said sampling time interval, said data acquisition system applies one of said positive gain offsets to intensity projection signals transmitted by said first photodiode comprised by said first detector element and applies one of said negative gain offsets to intensity projection signals transmitted by said first photodiode comprised by said second detector element.

10. A system in accordance with claim 9 wherein said gains have approximately equal and approximately constant magnitudes.

11. A system in accordance with claim 10 wherein each of said gains is applied in accordance with:

$$I \times (1 + dg(t))$$

where I is the intensity projection signal to which said gain is being applied and dg(t) is said gain offset.

12. A system in accordance with claim 8 wherein, for at least one said detector element, said sampling time interval is divided to comprise a first subinterval and a second subinterval.

13. A system in accordance with claim 12 wherein, for at least one said detector element, said data acquisition system applies said zero gain offset to intensity projection signals transmitted by said photodiodes.

14. A system in accordance with claim 12 wherein, for at least one said detector element, said data acquisition system applies one of said positive gain offsets to intensity projection signals transmitted by said first photodiode for the duration of said first subinterval and applies one of said negative gain offsets to intensity projection signals transmitted by said first photodiode for the duration of said second subinterval.

15. A system in accordance with claim 14 wherein said gains have approximately equal and approximately constant magnitudes.

16. A system in accordance with claim 15 wherein each of said gains is applied in accordance with:

$$I \times (1 + dg(t))$$

where I is the intensity projection signal to which said gain is being applied and dg(t) is said gain offset.

17. A system in accordance with claim 14 wherein said data acquisition system applies one of said negative gain offsets to intensity projection signals transmitted by said second photodiode for the duration of said first subinterval and applies one of said positive gain offsets to intensity projection signals transmitted by said second photodiode for the duration of said second subinterval.

18. A system in accordance with claim 17 wherein said gains have approximately equal and approximately constant magnitudes.

19. A system in accordance with claim 18 wherein each of said gains is applied in accordance with:

$$I \times (1 + dg(t))$$

where I is the intensity projection signal to which said gain is being applied and dg(t) is said gain offset.

20. A system in accordance with claim 7 wherein said processor is configured to estimate said z-derivative values in accordance with:

$$I \approx I_1 + I_2$$

$$\Delta z I_z' \approx \frac{(I_1 - I_2)}{\frac{1}{2} \delta g} - (I_1 + I_2)$$

where I is the intensity projection signal, $I_z'$ is the estimate of said z-derivative values, $I_1$ and $I_2$ are intensity projection signals sampled from one said detector element over said sampling time interval, and $\delta g$ is one of said gains.

21. A method for sampling z-derivative data in a computed tomography imaging system, the imaging system including at least one detector element including a scintillator, a first photodiode and a second photodiode, the scintillator optically coupled to the photodiodes, the imaging system configured to sample intensity projection signals over a sampling time interval, said method comprising the steps of:

acquiring intensity projection signals by means of at least one detector element;

sampling the intensity projection signals over the sampling time interval;

applying at least one gain to the intensity projection signals transmitted by at least one of the photodiodes for the duration of at least a portion of the sampling time interval; and determining z-derivative values from the intensity projection signals as affected by the gains.

22. A method in accordance with claim 21 wherein the detector elements include at least one detector element pair including a first detector element and a second detector element, and the step of applying at least one gain to the intensity projection signals transmitted by at least one of the photodiodes for the duration of at least a portion of the sampling time interval comprises the steps of:

applying a positive gain offset to intensity projection signals transmitted by the first photodiode of the first detector element; and applying a negative gain offset to intensity projection signals transmitted by the first photodiode of the second detector element.

23. A method in accordance with claim 22 wherein each gain offset has a magnitude and the magnitude of the positive gain offset is approximately constant and approximately equal to the magnitude of the negative gain offset.

24. A method in accordance with claim 23 further comprising the step of applying each of the gains in accordance with:

$$I \times (1+dg(t))$$

where I is the intensity projection signal to which the gain is being applied and dg(t) is the gain offset.

25. A method in accordance with claim 21 wherein the step of sampling the intensity projection signals over the sampling time interval comprises the step of dividing the sampling time interval into at least a first subinterval and a second subinterval.

26. A method in accordance with claim 25 wherein the step of applying at least one gain to the intensity projection signals transmitted by at least one of the photodiodes for the duration of at least a portion of the sampling time interval comprises the step of applying a zero gain offset to the intensity projection signals transmitted over the first subinterval and zero gain offset to the intensity projection signals transmitted over the second subinterval.

27. A method in accordance with claim 25 wherein, for intensity projection signals transmitted by at least one of the detector elements, the step of applying at least one gain to the intensity projection signals transmitted by at least one of the photodiodes for the duration of at least a portion of the sampling time interval comprises the steps of:

applying a positive gain offset to intensity projection signals transmitted by the first photodiode for the duration of the first subinterval; and applying a negative gain offset to intensity projection signals transmitted by the first photodiode for the duration of the second subinterval.

28. A method in accordance with claim 27 wherein each of the gains has a magnitude and the magnitude of the positive gain offset is approximately constant and approximately equal to the magnitude of the negative gain offset.

29. A method in accordance with claim 28 further comprising the step of applying each of the gains in accordance with:

$$I \times (1+dg(t))$$

where I is the intensity projection signal to which the gain is being applied and dg(t) is the gain offset.

30. A method in accordance with claim 27 wherein the step of applying at least one gain to the intensity projection signals transmitted by at least one of the photodiodes for the duration of at least a portion of the sampling time interval further comprises the steps of:

applying a negative gain offset to intensity projection signals transmitted by the second photodiode for the duration of the first subinterval; and applying a positive gain offset to intensity projection signals transmitted by the second photodiode for the duration of the second subinterval.

31. A method in accordance with claim 30 wherein each of the gains has a magnitude and the magnitude of the positive gain offset is approximately constant and approximately equal to the magnitude of the negative gain offset.

32. A method in accordance with claim 31 further comprising the step of applying each of the gains in accordance with:

$$I \times (1+dg(t))$$

where I is the intensity projection signal to which the gain is being applied and dg(t) is the gain offset.

* * * * *